United States Patent [19]
Lemoine et al.

[11] Patent Number: 5,965,127
[45] Date of Patent: Oct. 12, 1999

[54] **EXOCELLULAR POLYSACCHARIDE PRODUCED BY *STREPTOCOCCUS THERMOPHILUS***

[75] Inventors: Jérôme Lemoine, Lille, France; Jean-Richard Neeser, Savigny, Switzerland

[73] Assignee: Nestec S.A., Vevey, Switzerland

[21] Appl. No.: 09/065,735

[22] Filed: Apr. 24, 1998

[30] Foreign Application Priority Data

Jul. 5, 1997 [EP] European Pat. Off. ............... 97111379

[51] Int. Cl.$^6$ ................ A61K 35/74; A61K 31/715; C08B 37/00; C12P 19/04

[52] U.S. Cl. ..................... 424/93.44; 424/244.1; 536/123; 536/123.1; 514/54; 435/101; 435/72

[58] Field of Search ................... 536/123, 123.1; 514/54; 435/101, 72; 424/244.1, 93.44

[56] References Cited

FOREIGN PATENT DOCUMENTS 03 229 702  10/1991  Japan .

OTHER PUBLICATIONS

Lemoine et al, Appl. Environ. Microbiol. 63(9):3512–3518 (1997).

*Cell*, vol. 76, 597–598, Feb. 25, 1994, S. Barondes et al., "Galectins: A Family of Animal β–Galactoside–Binding Lectins".

*Glycobiology*, vol. 4, No. 1, pp. 5–12, 1994, R. Colin Hughes "Mac–2: a versatile galactose–binding protein of mammalian tissues".

*J. Exp. Med.*, vol. 177, Jan. 1993, 243–248, M. Truong et al. "Human Neutrophils Express Immunoglobulin E (IgE)–binding Proteins (Mac–2/εBP) of the S–Type Lectin Family: Role in IgE—dependent Activation".

*J. Exp. Med.*, vol. 178, Sep. 1993, 777–785, A. Wollenberg et al. "Human Keratinocytes Release the Endogenous β–Galactoside–binding Soluble Lectin Immunoglobulin E (IgE–Binding Protein) which Binds to Langerhans Cells Where It Modulates Their Binding Capacity for IgE Glycoforms".

*Oral Bacterial Adherence*, vol. 7, Mar. 1993, pp. 406–412, P.E. Kolenbrander et al., "Coaggregation: specific adherence among human oral plaque bacteria".

*Primary Examiner*—Francisco Prats
*Attorney, Agent, or Firm*—Pennie & Edmonds LLP

[57] ABSTRACT

The invention relates to a new isolated exo-polysaccharide originating from *Streptococcus thermophilus* consisting of essentially D-galactose, L-rhamnose and D-glucose in a molar ratio of 3:2:1, and optionally consisting of the following repeat structure. This polysaccharide may be used in flavor reactions, and for the preparation of a food, cosmetic or pharmaceutical composition intended for inhibiting β-galactoside specific lectins.

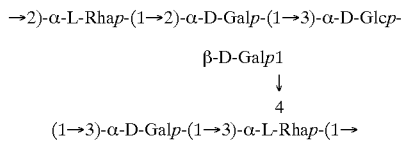

8 Claims, No Drawings

EXOCELLULAR POLYSACCHARIDE PRODUCED BY *STREPTOCOCCUS THERMOPHILUS*

The present invention relates to a new exocellular polysaccharide (EPS) originating from *Streptococcus thermophilus*.

STATE OF THE ART

The biological communication (the possibility for a cell to recognize a molecule or another cell) is a central phenomenon in pathological as well as in the normal state. Among the various mechanisms of molecular recognition between cells, and/or between cells and molecules, the binding of specific glycosidic structures by specialized proteins, called lectins, is today considered as a major molecular recognition system.

Dealing with a class of mammalian lectins recognizing galactose residues, membership in the galectin family requires fulfillment of two criteria: affinity for β-galactosides and significant sequence similarity in the carbohydrate-binding site, the relevant amino acid residues which have been determined (Barondes et al., Cell, 76, 598, 1994). Since galectins may be bound specifically and non-covalently to well-defined glycosidic sequences, β-gal-containing polysaccharides may thus be used in-vitro or in-vivo to inhibit specifically the binding of galectins and their receptors, an effect which may modulate many biological systems including pathological situations (EP699689; Hughes et al., Glycobiology, 4, 5–12, 1994; Truong et al., Journal of Experimental Medicine, 177, 243–248, 1993; Wollenberg et al., Journal of Experimental Medicine, 178, 777–785, 1993).

Such polysaccharides may also be used for inhibiting microbial β-galactoside specific lectins, for example those modulating coaggregations of human oral plaque bacteria. Indeed, proteinaceous surface molecules (called adhesins) on one plaque cell type recognize carbohydrate receptors on partner plaque bacteria in most of the coaggregations studied so far. Many of those coaggregations are known to be inhibitable by lactose or other β-galactoside derivatives. Among those, some are preferably inhibited by rhamnose containing polysaccharides (Kolenbrander et al., The FASEB Journal, 7, 406–412, 1993).

In addition, until now L-rhamnose was customarily manufactured by costly extraction using organic solvents from vegetable resources available only during their respective harvest periods. These include, for example, glycosides like rutin, hesperidin and naringin, which are found in the skins of oranges and grapefruits. The carbohydrate L-rhamnose has considerable potential as a preliminary stage for reaction flavors in the preparation of foodstuffs. Further untapped potential for L-rhamnose can also be seen in chemical synthesis. L-rhamnose may also be used in the manufacture of pharmaceutical substances like cardiac glycosides and means for treating tumours, for example.

Finally, there have been many prior studies upon polysaccharides produced by micro-organisms and, in recent years, there have been several reports of studies on the structure of exocellular polysaccharides obtained by lactic acid bacteria and on their biological activities. For instance, a polysaccharide consisting of galactose, glucose and N-acetylgalactosamine (2:1:1) may be obtained from the strains *Streptococcus thermophilus* CNCM I-733, CNCM I-734 and CNCM I-735 (see EP331564). In addition, EP750043 discloses the genes and proteins from *Streptococcus thermophilus* CNCM I-1590 involved in the biosynthesis of the above type of exopolysaccharide.

The aim of the present invention is to provide a new polysaccharide which can be used in reaction flavors, and which can be used to inhibit the binding between β-galactoside specific lectins and their receptors, i.e. to inhibit L-rhamnose specific bacterial coaggregation in the buccal cavity.

DESCRIPTION OF THE INVENTION

In the following description the expression "β-galactoside specific lectin" designates all carbohydrate-binding proteins specific for β-galactosides, from plant, mamalian, microbial and virus sources. Any β-galactoside specific toxin produced by microbes should also be considered as a lectin in the frame of the present invention.

The present invention concerns a new isolated exopolysaccharide originating from *Streptococcus thermophilus* consisting of essentially D-galactose, L-rhamnose and D-glucose in a molar ratio of 3:2:1, and preferably comprising the following repeat structure:

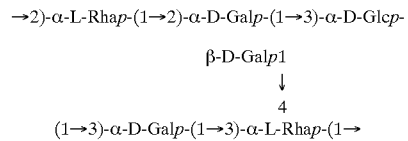

According to a preferred embodiment the EPS of the invention only possesses the above repeat structure.

A EPS according to the present invention may be naturally produced by *Streptococcus thermophilus* strains, in particular by the stain CNCM I-1878 which has been deposited under the Budapest Treaty in Jun. 20, 1997, at the Collection Nationale de Culture de Microorganismes (CNCM), 25 rue du docteur Roux, 75724 Paris, France.

Details about the strains with respect to its morphology and sugar fermentation pattern are as follows.

Morphology: isolated diplococcies or in form of short chain.

Sugar fermentation: glucose, lactose and sucrose.

The invention also has for object the use of this EPS for the preparation of a composition intended for inhibiting β-galactoside specific lectins, especially for inhibiting β-galactoside microbial lectins, i.e for inhibiting coaggregations of L-rhamnose-specific human oral plaque bacteria. According to a preferred embodiment such composition, comprising an effective amount of this EPS for inhibiting β-galactoside specific lectins, may be administered orally to a human in need thereof.

The invention also has for object the use of this polysaccharide in reaction flavors It is well known that in mild acidic conditions, glycosidic bounds involving L-rhamnose are the most sensitive ones. According, the EPS of the invention may be hydrolysed in especially mild conditions, i.e. pH about 2–4 and moderate heating of about 70–90° C., in such a way that at least one L-rhamnose residue by repeating unit is liberated. This mixture may then be further reacted with amino-acid containing materials, under suitable conditions (heating) which will convert free L-rhamnose into at least furaneol (by a three step reaction). Furaneol itself is responsible for a strong caramel-like flavour.

In addition, in the presence of sulfur-containing amino-acids (i.e. cystein), furaneol is known to be, partially or totally, converted into thiofuraneol which is responsible for a savoury meat flavour. Accordingly, the mixture containing liberated L-rhamnose thus may be also further reacted with amino-acid containing materials in the presence of sulfur-containing amino-acids.

The present invention also has for object a food, a cosmetic or a pharmaceutical composition comprising as additive an effective amount of this EPS for inhibiting β-galactoside specific lectins, especially for inhibiting β-galactoside microbial lectins, i.e for inhibiting coaggregations of L-rhamnose-specific human oral plaque bacteria. Such composition may be prepared by isolating the EPS followed by the addition of the isolated EPS to a food, a cosmetic or a pharmaceutical composition adapted for the purpose and method of consumption or application.

Isolation of the EPS according to the invention may require the removal of proteins and bacteria from a lactic fermented culture, for example of the strain CNCM I-1878, and then isolation of the EPS. Removal of proteins and bacteria may be achieved by precipitation with a solution of alcohol or trichloroacetic acid followed by centrifugation, whereas isolation of EPS may be achieved by precipitation with another solvent (acetone) followed by centrifugation, for example. If necessary, the EPS may be further purified by gel-filtration or with an affinity column, for example.

In the context of the present invention, isolation of the EPS according to the invention also encompasses any method of EPS production by fermentation followed by a concentration of the constituents in the medium. Concentration may thus be achieved by any method known to the skilled person, in particular by lyophilisation or spray-drying methods, for example (see U.S. Pat. No. 3,985,901, EP298605 or EP63438).

Finally, the present invention also has for object a food, a cosmetic or a pharmaceutical composition comprising a killed bacteria having produced in-situ the EPS according to the invention, or a live bacteria producing or having produced in-situ the EPS according to the invention.

The present invention is not to be limited in scope by the specific embodiments described herein. Indeed, various modifications of the invention, in addition to those described herein, will become apparent to those skilled in the art from the foregoing description. Such modifications are intended to fall within the scope of the claims. Various publications are cited herein, the disclosures of which are incorporated by reference in their entireties to the extent necessary for understanding the present invention. In the following description, the percentages are given by weight except where otherwise stated. The following examples are preceded by a description of the EPS characterisation and purification according to the invention.

BACTERIA STRAIN AND FERMENTATION CONDITIONS

*Streptococcus thermophilus* CNCM I-1878 is a ropy strain from the Nestle strain collection. The growth medium was skim milk powder reconstituted at 10% and heat-treated (115° C., 35 min) for sterilization (9 parts), plus an amino acid mixture (1 part; 495 mg/l Ala, 343 mg/l Arg, 682 mg/l Asp, 59 mg/l Cys, 1229 mg/l Glu, 759 mg/l Gly, 153 mg/l His, 215 mg/l Iso, 470 mg/l Leu, 565 mg/l Lys, 122 mg/l Met, 255 mg/l Phe, 436 mg/l Pro, 68 mg/l Ser, 170 mg/l Thr, 61 mg/l Try, 304 mg/l Val) adjusted to pH 5.0 with 1M NaOH and filtered for sterilization. The fermentation was carried out in a 1 liter-scale fermentor for 24 h at 40° C. with an inoculum of 1%. The pH was maintained at 5.5 by using 2N NaOH and a stirring rate of 60 RPM.

EXTRACTION OF THE POLYSACCHARIDE

The removal of proteins and bacteria from the spent fermented cultures was achieved by the addition of an equal volume of a solution of trichloroacetic acid (TCA, 40%), followed by centrifugation (17,000×g, 20 min). Then, the same volume of acetone was added to the supernatant fraction to precipitate the EPS, which was finally collected by centrifugation (17,000×g, 20 min). Such precipitated EPS fractions were dissolved in distilled water and the pH was adjusted to 7.0 with a sodium hydroxide solution. After dialysis against distilled water (16 h), insoluble material was removed by ultracentrifugation (110,000×g, 1 h) and the EPS was lyophilized. Total neutral sugar content of this crude dehydrated EPS was determined by the phenol-sulphuric acid method (Dubois et al., Anal. Chem., 28, 350–356, 1956). This extraction yielded 105 mg of EPS.

SIZE OF THE EXOPOLYSACCHARIDE

The gel-filtration chromatography was conducted to confirm the purity and to estimate the molecular weight of the polysaccharide using a FPLC system (Pharmacia) with a Superose 6 column (10 cm×30 cm). Samples (200 μl) containing 200–400 μg dehydrated polysaccharide were applied onto the column, and eluted with 50 mM phosphate buffer at pH 7.2 at the rate of 0.5 ml/min. Fractions of 1.0 ml were collected and the total neutral sugar content in each fraction was determined by the phenol-sulphuric acid method. EPS was eluted at the exclusion limit (approximately $2 \times 10^6$ Da).

MONOSACCHARIDE COMPOSITION

Monosaccharide composition was first determined by gas-liquid chromatography (GLC) of O-methyloxime acetate derivatives obtained after acid hydrolysis of the polysaccharide (1 h, 125° C.) in a 4 N trifluoroacetic acid (TFA) solution (Neeser et al., Anal. Biochem., 142, 58–67, 1984). Independently, polysaccharide samples (0.1 mg) were methanolysed (methanolic 0.5N HCl, 80° C., 24 h), and the trimethylsilylated N-reacetylated methyl glycosides were analysed using a Varian 3400 gas chromatograph (temperature program: 120° C. to 240° C. at 2° C./min) on a BP1 fused-silica capillary column (25 m×0.32 mm, SGE). The absolute configuration of the monosaccharides was also determined by GLC, using the trimethylsilylated N-reacetylated (-)-2-butyl glycoside derivatives. Results show the presence of D-galactose, D-rhamnose and D-glucose in a molar ratio of 3:2:1.

NUCLEAR MAGNETIC RESONANCE SPECTROSCOPY

The 400 MHz $^1$H-NMR experiments were performed with a Bruker AM-400 wide bore spectrometer equipped with a 5 mm $^1$H/$^{13}$C dual probe head, operating in the pulsed Fourier transform mode and controlled by an Aspect 3000 computer. All spectra were obtained at a probe temperature of 333° K. For one-dimensional spectra, a 90-degree pulse of 10.6 μs and 1 s recycle delay were used. The chemical shifts are given relative to the signal of the methyl group of acetone (δ 2.225 for $^1$H and 31.55 for $^{13}$C).

The 2D-homonuclear COSY 45, COSY with simple, double, and triple relay transfers were performed by means of the standard Bruker pulse program library, or the programs given by B. Perly (CEA Saclay, France). For all Relayed Coherence Transfer (RTC) experiments, refocusing delays of 35 ms were chosen and the relaxation delay was 2 s. In all these experiments, the spectral width was 1840 Hz, the $^1$H 90-degree pulse was 10.6 μs; 256 W×2K FID data matrices were acquired, which were zero-filled prior to Fourier transform, to obtain a 1K×2K spectral data matrix; a sine-bell squared filter function was used in both dimensions.

The 2D-$^{13}$C/$^1$H COSY experiments were performed with simultaneous suppression of $^1$H homonuclear couplings by means of the standard Bruker pulse program XHCORRD. Refocusing delays were adjusted to an average $^1J_{C,H}$ coupling constant of 150 Hz. $^1$H and $^{13}$C 90-degree pulse width were 10.6 and 6 μs, respectively. The relaxation delay was 0.8 s. A 128 W×4K FID data matrix was acquired, which was zero-filled prior to Fourier transform, to obtain a 512 W×4K spectral data matrix. An exponential function (LB=1 Hz) for $^{13}$C-subspectra and a sine-bell filter function for $^1$H-spectra were applied to enhance the signal to noise ratio.

For clarity in the presentation of the NMR data, the numbering of the sugar residues (capital letters) and protons of each residue (arabic numerals) deduced from the assignment procedure will be used here in advance:

relayed COSY spectra (one and two relais successively). These sugar units were respectively identified according to the magnitude of the $^3J_{H,H}$ values: residues B, D and F were identified as galacto compounds from the small $J_{3,4}$, and $J_{4,5}$ exhibited by residue C indicated a gluco configuration. Resonances corresponding to H-6 of rhamnosyl residues A and E were correlated to their anomeric protons via the H-6→H-5→H-4→H-3 and the H-3→H-2→H-1 connectivities depicted on the relayed COSY spectrum. Moreover, the α-anomericity of these rhamnosyl residue was latter confirmed by the observation of their C-5 atom resonances at 69~70 ppm (see Table 1).

Owing to the correlation peaks observed on the relayed COSY spectrum, a complete assignment of protons was performed (Table 2). After having reported these data on the HMQC spectrum, all carbon resonances revealed the linkage position: a 2-substituted αRhap (E), a 2-substituted αGalp (D), a 3-substituted αGlcp (C), a 3-substituted αGalp (B), a 3,4-disubstituted αRhap (A) and a non-reducing terminal βGalp (F).

Finally, the repeating unit sequence was established and the linkage positions confirmed with the aid of ROESY

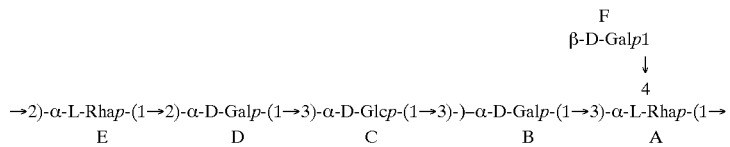

The occurrence of a hexasaccharidic repeating unit was established by the $^1$H and $^{13}$C NMR data from the native polysaccharide, that revealed six anomeric protons and carbons (tables 1 and 2).

The $^3J_{1,2}$ values were measured on the two step-relayed COSY spectrum which revealed three α and one β hexosyl residues, together with two rhamnose units ($^3J_{1,2}$~1 Hz).

The six sugar unit residues were identified on the basis of their vicinal proton constant values with the aid of the 2 D correlation spectroscopy. The ROEs for the corresponding transglycosidic anomeric/aglyconic proton pairs were found for the following sugar units:

H-1 Gal(F)→H-4 Rha(A); H-1 Gal(B)→H-2,H-3 Rha(A); H-1Glc(C)→H-4 Gal(B); H-1 Gal(D)→H-2,H-3,H-4 Glc(C); H-1Rha(E)→H-2 Gal(D).

TABLE 1

$^{13}$C chemical shifts for the native polysaccharide

| | Chemical shift (δ) in residue | | | | | |
|---|---|---|---|---|---|---|
| Carbon | E →2α-L-Rhap | D →2-α-D-Galp | C →3-α-D-Glcp | B →3-α-D-Galp | A →3(4)-α-L-Rhap | F β-D-Galp1 |
| C-1 | 100.9 | 98.7 | 96.5 | 94 | 102.8 | 103.7 |
| C-2 | 79.7 | 75 | 70.9 | 67.6 | 66.1 | 71.9 |
| C-3 | 70.8 | 71 | 79.5 | 73.8 | 75.7 | 74 |
| C-4 | 73.2 | 70.6 | 70.9 | 69.2 | 76.4 | 69.7 |
| C-5 | 70.1 | 71.7 | 72.5 | 71.7 | 69 | 76 |
| C-6 | 17.6 | 61.9 | 61.2 | 61.9 | 18 | 62.1 |

TABLE 2

$^1$H chemical shifts for the native polysaccharide

| | Chemical shift (δ) in residue | | | | | |
|---|---|---|---|---|---|---|
| Proton | E →2α-L-Rhap | D →2-α-D-Galp | C →3-α-D-Glcp | B →3-α-D-Galp | A →3(4)-α-L-Rhap | F β-D-Galp1 |
| H-1 | 5.282 | 5.497 | 5.159 | 5.306 | 5.057 | 4.687 |
| H-2 | 4.098 | 4.000 | 3.766 | 4.078 | 4.388 | 3.552 |
| H-3 | 4.931 | 4.097 | 4.019 | 4.171 | 4.181 | 3.697 |

TABLE 2-continued $^1$H chemical shifts for the native polysaccharide

| | Chemical shift (δ) in residue | | | | | |
|---|---|---|---|---|---|---|
| Proton | E →2α-L-Rhap | D →2-α-D-Galp | C →3-α-D-Glep | B →3-α-D-Galp | A →3(4)-α-L-Rhap | F β-D-Galp1 |
| H-4 | 3.514 | 4.073 | 3.721 | 4.234 | 4.019 | 3.966 |
| H-5 | 3.858 | 4.313 | 4.069 | 4.262 | 3.892 | 3.686 |
| H-6 | 1.332 | 3.79 | 3.84 | 3.81 | 1.369 | 3.85 |
| H-6' | | 3.79 | 3.84 | 3.81 | | 3.80 |

EXAMPLE 1
Set-style acidifed milk

Set-style acidifed milk comprising the *S-thermophilus* CNCM I-1878 strain was obtained by the following process. To a whole milk comprising 3.7% fat, 2.5% skimmed milk powder and 1% yeast extract were added. 40 liters of this milk were pasteurized at 92° C. for six minutes, homogenized at 75° C. and 150 bars (two levels) and cooled at a temperature around 42° C. The freeze-dried *S. thermophilus* CNCM I-1878 strain was reactived with several successive cultures in a sterile MSK medium (skimmed milk powder reconstituted at 10%, comprising 0.1% of a commercial yeast extract). The sterilized milk was inoculated with 1% of the culture of *S. thermophilus* strain taken at the medium coagulation stage. The milk was incubated at 42° C. until reaching a pH around 4.65, and then cooled at a temperature of 4° C.

EXAMPLE 2
Purification of the EPS

To a whole milk comprising 3.7% fat, 2.5% skimmed milk powder and 1% yeast extract were added. 40 liters of this milk were pasteurized at 92° C. for six minutes, homogenized at 75° C. and 150 bars (two levels) and cooled at a temperature around 42° C. The freeze-dried *S. thermophilus* CNCM I-1878 strain was reactivated with several successive cultures in a sterile MSK medium (skimmed milk powder reconstituted at 10%, comprising 0.1% of a commercial yeast extract). The sterilized milk was inoculated with 1% of the culture of *S. thermophilus* strain taken at the medium coagulation stage. The milk was incubated at 40° C. The pH was maintained at 5.5 by using 2N NaOH and a stirring rate of 60 rpm during 24 hours.

The removal of proteins and bacteria from the fermented culture was achieved by the addition of an equal volume of a solution of trichloroacetic acid (TCA, 40%), followed by centrifugation (17,000×g, 20 min). Then, the same volume of acetone was added to the supernatant fraction to precipitate the EPS, which was finally collected by centrifugation (17,000×g, 20 min). Such precipitated EPS fractions were dissolved in distilled water and the pH was adjusted to 7.0 with a sodium hydroxide solution. After dialysis against distilled water (16 h), insoluble material was removed by ultracentrifugation (110,000×g, 1 h) and the EPS was lyophilized.

EXAMPLE 3
Whey milk

Whey milk comprising the *S. thermophilus* CNCM I-1878 strain was obtained by the following process. A sweet lactoserum powder was reconstituted at 12.5% in water. 1% yeast extract was added. 40 liters of this whey were pasteurized at 92° C. for six minutes, homogeneized at 75° C. and 150 bars (two levels) and cooled at a temperature around 42° C. The freeze-dried *S. thermophilus* CNCM I-1878 was reactived with several successive cultures in a sterile MSK medium (skimmed milk powder reconstituted at 10%, comprising 0.1% of a commercial yeast extract). The sterilized milk was inoculated with 1% of the culture of the *S. thermophilus* strain taken at the medium coagulation stage. The whey milk was incubated at 42° C. until reaching a pH around 4.65, and then cooled at a temperature of 4° C. Finally, the fermented culture was spray-dryed according to the method described in EP96201922.0 (Nestlé).

EXAMPLE 4
Pharmaceutical composition for buccal hygiene

| CHEMICAL NAME | TRADE NAME | % WEIGHT |
|---|---|---|
| PHASE A | | |
| PEG-40 Hydrogenated castor oil | Cremophor RH 40 | 0.1 |
| Flavour | Strawberry E 2226 | 0.04 |
| Flavour | Raspberry | 0.1 |
| PHASE B | | |
| Sodium Cyclamate | Sodium Cyclamate | 0.1 |
| Exopolysaccharide preparation from example 2 | | 0.50–5.00 |
| Demineralized water | | 94.66–99.16 |
| TOTAL | | 100 |

EXAMPLE 5
Cosmetic composition for skin hygiene

| | % WEIGHT |
|---|---|
| OIL PHASE | |
| BRIJ 721 (Steareth 21) | 4 |
| Cetyl alcohol | 0.04 |
| Mineral oil | 0.1 |
| Propyl parahydroxybenzoate | |
| WATER PHASE | |
| CARBOPOL 934 (Carbomer 934) | 0.1 |
| Sodium hydroxide (solution at 10%) | 0.1 |
| Methyl parahydroxybenzoate | 0.18 |
| Exopolysaccharide preparation from example 2 | 0.50–5.00 |
| Demineralized water | 75.60–80.10 |
| TOTAL | 100 |

EXAMPLE 6
Pharmaceutical composition for gastroenterological usage

A pharmaceutical composition was obtained as a capsule which was made with gelatine and water, and which contained from 5 to 50 mg of the exopolysaccharide according to example 2. Alternatively, powdered tablet formulations can be obtained directly from the acidified cultured milks described above, in examples 1 and 3, by freeze-drying these fermented milks and pressing the resulting powder in a form of tablets.

EXAMPLE 7

Flavour reaction

The isolated EPS of example 2 is hydrolysed in very mild conditions, i.e. pH about 2–4 and moderate heating of about 90° C., in a medium containing amino-acids proteins and/or polypeptides, during a time sufficient for at least liberating one rhamnose residue by repeating unit which will generate furaneol and/or thiofuraneol.

We claim:

1. An isolated polysaccharide originating from *Streptococcus thermophilus* consisting of essentially D-galactose, L-rhamnose and D-glucose in a molar ratio of 3:2:1.

2. The isolated polysaccharide according to claim 1 consisting of the following repeat structure

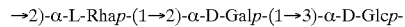
→2)-α-L-Rha*p*-(1→2)-α-D-Gal*p*-(1→3)-α-D-Glc*p*-

-continued

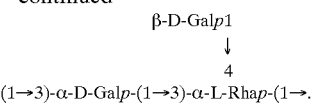

β-D-Gal*p*1
↓
4
(1→3)-α-D-Gal*p*-(1→3)-α-L-Rha*p*-(1→.

3. A composition comprising the polysaccharide according to claim 1, wherein said composition inhibits the binding of β-galactoside specific lectins.

4. The composition according to claim 3, wherein said composition inhibits the binding of β-galactoside specific microbial lectins.

5. A method of producing a flavoring agent comprising hydrolyzing the polysaccharide according to claim 1.

6. A food, a cosmetic or a pharmaceutical composition comprising as additive the polysaccharide according to claim 1, wherein said composition inhibits β-galactoside specific lectins.

7. The food, cosmetic or pharmaceutical composition according to claim 6, which comprises 0.5 to 5% by weight of the polysaccharide.

8. A food, a cosmetic or a pharmaceutical composition, intended for inhibiting β-galactoside specific lectins, comprising a killed bacteria having produced in-situ the EPS according to claim 1, or a live bacteria producing or having produced in-situ the EPS according to claim 1.

* * * * *